(12) United States Patent
Brehm et al.

(10) Patent No.: US 12,324,874 B2
(45) Date of Patent: Jun. 10, 2025

(54) CONNECTION ELEMENT AND CONNECTION SYSTEM FOR A BLOOD TREATMENT DEVICE

(71) Applicant: FRESENIUS MEDICAL CARE DEUTSCHLAND GMBH, Bad Homburg (DE)

(72) Inventors: Winfried Brehm, Hofheim (DE); Rafael Sterzer, Schweinfurt (DE); Paul Seit, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 346 days.

(21) Appl. No.: 17/907,981

(22) PCT Filed: Feb. 22, 2021

(86) PCT No.: PCT/EP2021/054272
§ 371 (c)(1),
(2) Date: Aug. 30, 2022

(87) PCT Pub. No.: WO2021/180450
PCT Pub. Date: Sep. 16, 2021

(65) Prior Publication Data
US 2023/0106677 A1    Apr. 6, 2023

(30) Foreign Application Priority Data

Mar. 11, 2020 (DE) .................... 10 2020 106 590.6

(51) Int. Cl.
*F16L 39/00* (2006.01)
*A61M 1/14* (2006.01)
*A61M 1/16* (2006.01)

(52) U.S. Cl.
CPC ............ *A61M 1/152* (2022.05); *A61M 1/168* (2013.01); *F16L 39/00* (2013.01); *F16L 2201/44* (2013.01)

(58) Field of Classification Search
CPC ......... F16L 39/00; F16L 39/02; F16L 39/005; F16L 2201/44; A61M 1/152;
(Continued)

(56) References Cited

U.S. PATENT DOCUMENTS

2003/0168120 A1    9/2003 Brehm et al.
2010/0270792 A1    10/2010 Lauer
(Continued)

FOREIGN PATENT DOCUMENTS

DE    102009024575 A1    12/2010
DE    102013001438 B4    8/2017
(Continued)

OTHER PUBLICATIONS

International Search Report and Written Opinion issued in corresponding International Patent Application No. PCT/EP2021/054272 (with English translation of International Search Report) mailed Apr. 30, 2021 (14 pages).

Primary Examiner — Aaron M Dunwoody
(74) Attorney, Agent, or Firm — Kilyk & Bowersox, P.L.L.C.

(57) ABSTRACT

The invention relates to a connection element (1) for a blood treatment device, in particular for a dialysis machine. The connection element (1) has here an inlet line (2), for letting in a fluid into the connection element (1), an outlet line (3), for letting a fluid out of the connection element (1), at least a first discharge line (21), for discharging a fluid from the connection element (1), wherein the first discharge line (21) is formed in a subsection (22) around the inlet line (2), and wherein the inlet line (2) and the first discharge line (21) are
(Continued)

open to a first end section (23) of the connection element (1), and the first end section (23) is fluidically connected with the subsection (22).

19 Claims, 6 Drawing Sheets

(58) Field of Classification Search
CPC .......... A61M 1/168; A61M 1/14; A61M 1/16; A61M 1/1621; A61M 1/1656; A61M 2205/14; A61M 2205/6018; A61M 2209/10; A61M 2209/00
USPC .................. 285/123.2, 124.1, 124.4
See application file for complete search history.

(56) References Cited

U.S. PATENT DOCUMENTS

| | | |
|---|---|---|
| 2013/0248629 A1 | 9/2013 | Brandl et al. |
| 2014/0175126 A1* | 6/2014 | Carlsson ............... A61M 39/10 |
| | | 222/145.5 |
| 2014/0213962 A1 | 7/2014 | Marterstock |

FOREIGN PATENT DOCUMENTS

| | | |
|---|---|---|
| EP | 2682608 A1 | 1/2014 |
| WO | 0016916 A1 | 3/2000 |
| WO | 2013135389 A2 | 9/2013 |
| WO | 2019086321 A1 | 5/2019 |

* cited by examiner

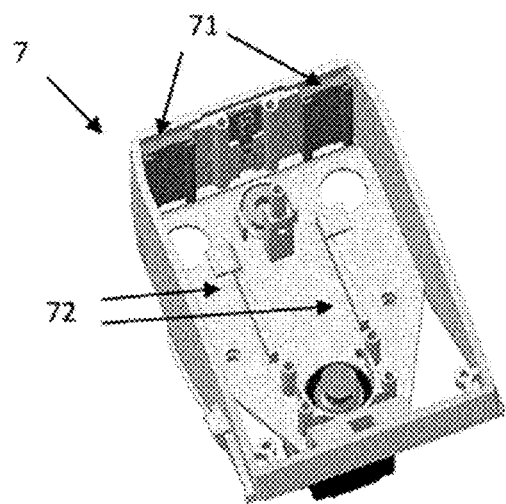
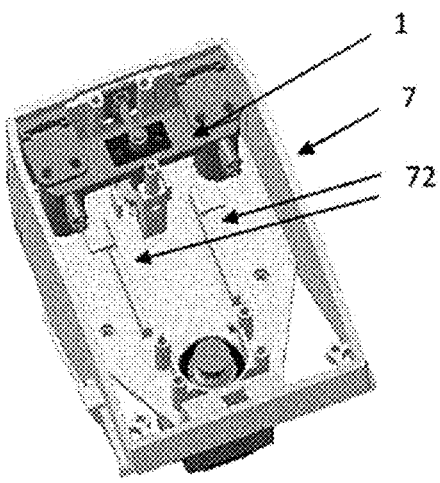
Fig. 4a · Fig. 4b
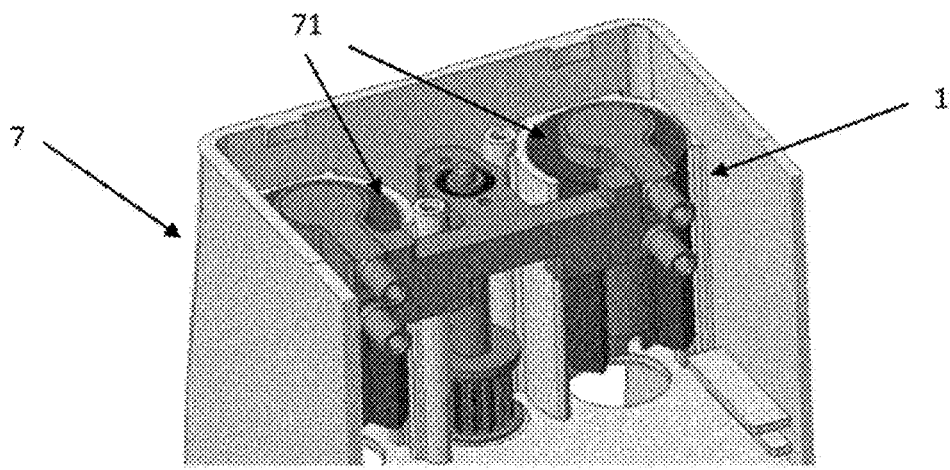
Fig. 5

CONNECTION ELEMENT AND CONNECTION SYSTEM FOR A BLOOD TREATMENT DEVICE

This application is a National Stage Application of PCT/EP2021/054272, filed Feb. 22, 2021, which claims priority to German Patent Application No. 10 2020 106 590.6, filed Mar. 11, 2020.

TECHNICAL FIELD

The present invention relates to a connection element for a blood treatment device, in particular a dialysis machine, a connection system for a blood treatment device, in particular a dialysis machine, and a connection method for the connection of a dry concentrate container.

BACKGROUND

The term "blood treatment device" is understood to mean inter alia a dialysis machine. Dialysis machines are frequently used in dialysis centres for the treatment of a chronic kidney disease.

During the dialysis, the patient's blood flows continuously through the blood chamber of the dialyser, whilst dialysing fluid flows continuously through the dialysing fluid chamber. For the production of dialysing fluid, prefabricated dialysing fluid concentrates can be used, which are diluted with water in the dialysis devices. In dialysis centres, dialysing fluid concentrates are made available either as a prefabricated product in cannisters, bags or cartridges, or are provided from a central tank via a ring line system.

Dialysing fluid concentrates which are made available centrally are easy to handle for the user, but they have the disadvantage that the dialysing fluid can not be coordinated individually to the requirements of the patient. Decentrally provided concentrates indeed permit an individual adaptation of the dialysing fluid to the patient, but they must be brought to the dialysis device for each individual dialysis treatment.

Bags or cartridges which are filled with a pulverulent dialysing fluid concentrate are used in dialysis for the production of a fluid dialysis concentrate. The concentrate bags or cartridges contain a quantity of pulverulent dialysing fluid concentrate which is sufficient for a single dialysis treatment. The bags or cartridges are filled with bicarbonate. Commercially available bicarbonate bags contain 650 to 950 g sodium bicarbonate. Firstly, a fluid bicarbonate concentrate is produced from the pulverulent bicarbonate concentrate. For the production of the dialysing fluid, a further acid concentrate is required, which is provided in a cannister or by a central supply. Bicarbonate concentrate and acid concentrate are then mixed with water to form the finished dialysing fluid.

The dialysis machine has, furthermore, a water connection, via which pure water is supplied. In the dialysis machine, the desired mixing of pure water with the corresponding concentrate subsequently takes place.

The provision of the fluid concentrate via concentrate containers entails various challenges, because the concentrate containers are heavy and therefore laborious for the nursing staff to handle. In addition, for the provision of the concentrate, suction wands of the dialysis machine must be introduced into the concentrate containers, which are inserted into the dialysis machine again after a treatment for cleaning. This handling of the concentrate containers is therefore time-intensive and can lead to a lengthening of the pauses between the individual treatments.

Alternatively, the concentrate can also be fed via a central supply and a corresponding central supply connection on the dialysis machine. However, this presupposes a corresponding equipping of the clinic, and can entail disadvantages with regard to the flexibility of the concentrate which is available and the maintenance effort of the lines which are operated for this.

From EP 1 344 550 A1 a connector is known for connecting a concentrate bag, which is filled with dry concentrate and can be mounted on a dialysis machine. Also in this type of concentrate supply, particular steps are necessary between the treatments. Therefore, a contamination protection arranged on the concentrate bag must be removed manually, the concentrate bag must be inserted, i.e. connected, into the corresponding mount on the dialysis machine and finally connected with the dialysate circuit.

The connection of the concentrate bag takes place in the prior art mostly from below. This means that the concentrate bag is fitted on connection sockets. After the treatment, the concentrate bag is lifted from the connection sockets. In so doing, residual fluid which is still present in the connection points of the concentrate bag can easily drip onto the floor.

Here, however, residual fluid of the bicarbonate solution can also lead to deposits at the connection sockets of the dialysis machine. This is caused by calcium- and magnesium salts. Through the configuration of the downwardly open connection points, this residual fluid can drip into the connection sockets of the dialysis machine and can cause the deposits there. These can lead, inter alia, to damage to sealing rings.

As described, the concentrate bag must be disconnected and removed from the dialysate circuit after a treatment. Only after the removal can a cleaning programme be started on the dialysis machine. The surface cleaning of the dialysis machine can only be carried out after the removal of the concentrate bag by the nursing staff.

In addition to high safety requirements, the time aspect plays a particular role in dialysis treatment, particularly in dialysis centres.

As sufficient time is to be available for the actual treatment, in particular the time between the treatments is subject to a constant time optimization. As described above, between the treatments, in addition to the preparation of the patient, the preparation of the dialysis machine for the next treatment through steps such as the provision of the required concentrate containers or disinfecting of the dialysis machine, takes time.

The present application is therefore based on the problem of making possible a connection of a concentrate bag on a blood treatment device which permits an improved handling and/or saving of time for the user, and at the same time guarantees the safety of the patient by, inter alia, an easy cleaning being possible.

SUMMARY OF THE INVENTION

The problem forming the basis of the invention is solved by a connection element for a blood treatment device according to claim 1, by a connection system for a blood treatment device according to the claims, and by a connection method according to the claims. Advantageous further developments and embodiments are the subject of the dependent claims.

According to the invention, a connection element is formed which has an inlet line for letting a fluid into the connection element, an outlet line, for letting a fluid out from the connection element. Furthermore, at least a first discharge line can be formed for discharging a fluid out from the connection element. The first discharge line can be formed in a subsection around the inlet line. The inlet line and the first discharge line can be open to an end section of the connection element, and the end section can be fluidically connected with the subsection.

The first discharge line can be identical here to the inlet line and/or to the outlet line. Here, at an end of the inlet line and/or outlet line lying opposite a dialysis machine or respectively a dialysis machine connection, by provision of a cleaning device, for example a blind hole, into which respectively the inlet line and outlet line can be introduced, an accumulation of the cleaning fluid can be achieved. After a certain time, the cleaning fluid can be discharged again through the inlet line and/or outlet line. Alternatively, a connecting duct can be formed in the cleaning device between the inlet line and the outlet line. Here, the cleaning fluid can be fed via one of the inlet line and/or outlet line. The other of the two lines is blocked off, for example by a valve. Thereby, the cleaning fluid is accumulated in both inlet- and outlet lines. Here, also, a discharging can take place via one or both inlet line and/or outlet line after a particular time.

The discharge line can also be formed around the inlet line and/or outlet line and can be connected with a connection line formed in the cleaning device, so that fluid washes around the inlet and/or outlet opening via the discharge line and is discharged further via the connection line.

The inlet line and outlet line can be formed at least partially cylindrically in their internal diameter. Also, the inner contour can be formed in a conically tapering manner or in a step-like manner.

According to a further development, the connection element can have, furthermore, a second discharge line for discharging a fluid out from the connection element. Here, the second discharge line can be formed in a second subsection around the outlet line. The outlet line and the discharge line can be open to an end section of the connection element and the end section can be fluidically connected with the subsection.

According to a further development of the connection element, the inlet line and/or outlet line and/or the first and second discharge line can be arranged in the connection element in such a way that a deflection of the fluid direction in the connection element, preferably by 120 to 70 degrees, more preferably of 110 to 80 degrees, particularly preferably of substantially 90 degrees, is able to be achieved.

According to a further development, the connection element can have, furthermore, a middle section, and a first extension in which the discharge line is formed around the inlet line, which first extension extends from a first end of the middle section in a first direction from the middle section, a second extension, in which the second discharge line is formed around the outlet line, which second extension extends from a second end, opposite the first, of the middle section in the first direction, preferably parallel to the first extension, from the middle section.

The first extension and/or the second extension can be formed here in a cylindrical shape. Also, the first and/or second extension can be formed conically or in a step-like manner and extendable in a telescope-like manner.

The first and/or second extension can extend from a middle section in a first direction, preferably substantially perpendicularly, from the middle section.

According to a further development, the connection element can have furthermore at least two, preferably three or four, more preferably four, preferably cylindrical, projections, preferably running parallel to one another. Here, the inlet line and the first discharge line can extend each in a projection from the first end of the middle section in a second direction, different from the first. In addition, the outlet line and the second discharge line can extend each in a projection from the second end of the middle section in the second direction. The at least one projection of the at least one discharge line can extend in a direction from the connection element which is different from the direction in which the projection of the inlet line and/or outlet line extends. In addition, the inlet line and outlet line can extend in different directions.

According to a further development, the connection element can have, furthermore, guide elements for the movable, preferably linearly displaceable, connection with a guide device.

The guide elements can be formed here integrally with the connection element or can be mounted thereon by screwing, gluing or welding. The guide elements can be track elements which are inserted in tracks and can be arranged so as to be linearly displaceable therein.

According to a further development, the connection element can have, furthermore, a positioning element. The positioning element can project from the middle section in a third direction, different from the first and second. In other words, the positioning element can project in the direction of the guide elements from the connection element. The positioning element can be an extension formed integrally on the connection element, for example a rectangular or cylindrical extension. The positioning element can project from the connection element in such a way that, with a linear moving of the connection element, it can interact with a light barrier. Alternatively, the positioning element can be a Hall sensor.

According to the invention, the connection system has a connection element, preferably according to one of the previously mentioned aspects, a housing, in which the connection element is movably arranged. Furthermore, the connection system can have a cleaning element which is arranged preferably movably in the housing. The cleaning element can be arranged outside the housing. The connection system has, furthermore, at least a first drive unit for moving the connection element and/or the cleaning element, and a control unit for actuating the at least first drive unit. Here, the connection element and/or the cleaning element can also be configured so as to be manually displaceable.

According to a further development, the connection system can have, furthermore, connection guides which are arranged in the housing, on which the connection element is movable between several, preferably three, positions. Furthermore, cleaning guides can be arranged, preferably in the housing, on which cleaning guides the cleaning element is movable between several, preferably two, positions.

According to a further development, the connection system can have, furthermore, at least one position sensor in the housing, preferably a light barrier, by means of which the position of the connection element and/or of the cleaning element is able to be detected.

According to the invention, a connection method for the connection of a dry concentrate container has the following steps. Here, a housing can have a connection element, preferably according to one of the preceding aspects, which is movable in the housing on a first straight line. The connection element can have two extensions, and a cleaning element, movable preferably in the housing on a second straight line, substantially perpendicular to the first straight line, in which cleaning element a first and a second line element are formed. The connection element can have the steps of moving the connection element on the first straight line for the formation of a cleaning position, wherein in the cleaning position the first and second extension of the connection element are in engagement with the first and second line element of the cleaning device.

The first and second line elements here can be blind bores or respectively blind holes. The line elements can also be through-bores and/or a connecting line can be formed between the first and second line element. The movement steps of the movement of the connection element and/or of the cleaning device can be carried out here automatically, for example by a drive unit, or by manual actuation by a nursing staff member. Likewise, also only the cleaning device or only the connection element can be actuated manually.

According to a further development, the connection method can furthermore have a movement of the connection element on the first straight line, movement of the cleaning device on the second straight line, movement of the connection element on the first straight line for the formation of the connection position, wherein in this connection position the first and second extension project from the housing.

According to a further development, the connection method can have furthermore an arranging of a container, preferably filled with dry concentrate, on the housing, when the connection element is in the cleaning position, a detecting as to whether a concentrate container is provided for connection, a moving of the connection element on the first straight line into the connection position, and a connecting of the container with the first and second extension of the connection element, so that a fluidic connection is produced.

According to a further development, the connection method, wherein the connection element is able to be fluidically connected with a blood treatment device, can have, furthermore, a moving of the connection element on the first straight line in a first direction, a moving of the cleaning element on the second straight line, a moving of the connection element on the first straight line in an opposite direction to the first direction for the formation of the cleaning position, so that the first and second extension are received respectively in the first and second line element of the cleaning device, and a cleaning of the first and second extension in the first and second line element.

According to the invention, furthermore a use of a connection element according to one of the preceding aspects is provided in a blood treatment device.

Through the connection element and the connection system, it is possible to connect a concentrate bag easily, i.e. with few handling steps, with a blood treatment device, in particular a dialysis machine. In particular, a concentrate bag can be mounted on the blood treatment device whilst a cleaning step of the connection sockets is still taking place. Through the configuration of the connection element and connection system, it is possible, in addition, to guarantee the safety of the patient.

The features and functions of the present invention which are described above, and further aspects and features are described further below with the aid of a detailed description of preferred embodiments with reference to the enclosed figures. In the figures, identical features/elements and features/elements with the same function are designated by the same reference numbers.

BRIEF DESCRIPTION OF THE DRAWINGS

There are shown here:
FIGS. 4a and 4b partial views of the connection system according to the first embodiment;
FIG. 5 a partial view of the connection system according to a second embodiment.

DETAILED DESCRIPTION OF AN EXAMPLE EMBODIMENT

Figure 1:
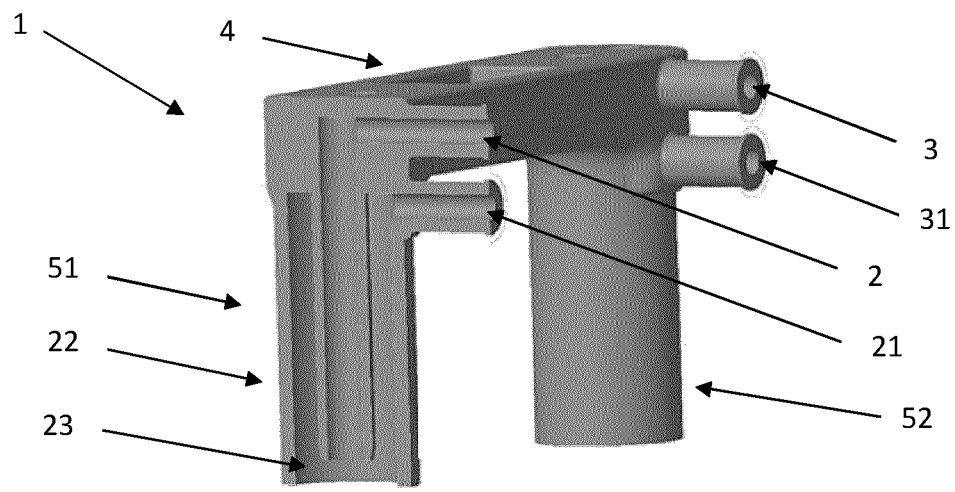
FIG. 1 a perspective schematic diagram of a connection element according to a first embodiment.

With reference to FIG. 1, a first embodiment will be explained below. FIG. 1 shows here a perspective schematic diagram of a connection element 1 according to a first embodiment. The connection element 1 has an inlet line 2. Via this inlet line 2, pure water can be introduced from a dialysis machine into the connection element 1 and can be introduced via the connection element 1 into a concentrate bag mounted on the dialysis machine. The concentrate bag, which is not illustrated here, can be filled here with bicarbonate in the form of a dry powder. The inlet line (2) is for letting in a fluid into the connection element (1), and an outlet line (3) is provided for letting a fluid out of the connection element (1). At least a first discharge line (21) is provided for discharging a fluid from the connection element (1), wherein the first discharge line (21) is formed in a subsection (22) around the inlet line (2). The inlet line (2) and the first discharge line (21) are open to a first end section (23) of the connection element (1), and the first end section (23) is fluidically connected with the subsection (22).

The pure water flowing into the concentrate bag via the connection element 1 mixes in the concentrate bag with the dry powder. The concentrate solution which has resulted by the mixing can subsequently flow out from the connection element 1. For this, the connection element 1 has an outlet line 3. The inlet line 2 and the outlet line 3 can be formed here parallel to one another and can be open in the same direction. In the inlet line 2, the inflowing fluid is deflected. For example, as shown in this embodiment, the fluid is deflected through 90 degrees. The connection element 1 has, furthermore, a first discharge line 21.

Figure 2:
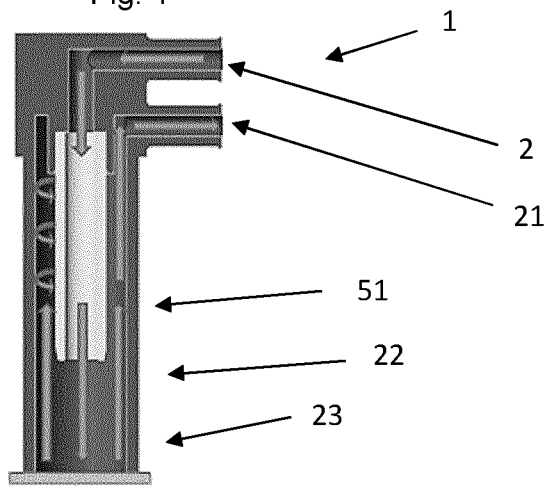
FIG. 2 a sectional view of the connection element according to a second embodiment.

The first discharge line 21 is formed here in a first subsection 22 around the inlet line 2. As illustrated in FIG. 1, the discharge line 21 can be a hollow cylinder in which the inlet line 2 partially extends. When the connection element 1, as shown in FIG. 2, is moved into a cleaning device 8, i.e. is not connected with a concentrate bag, a cleaning of the inlet line 2 can take place through the first discharge line 21. FIG. 2 shows here a sectional view of the connection element 1 according to a second embodiment. A cleaning of the connection element 1 is carried out for example after a dialysis treatment. Here, the entire dialysate circuit is flushed, wherein disinfectant is introduced here into the dialysate circuit. When the connection element 1 is moved into the cleaning device 8 for cleaning, the fluid, now disinfectant, can be diverted in the cleaning device 8 and can flow out from the connection element 1 through the first discharge line 21. The fluid flow is illustrated in FIG. 2. Here, the disinfectant flushes the inlet line 2, because the disinfectant is discharged via the discharge line. For residual fluid remaining in the cleaning device 8 can in [ . . . ]

As the first discharge line 21 extends around the outer circumference of the inlet line 2, it can be ensured that this is disinfected sufficiently. A second discharge line 31 is also formed around the outlet line 3 in an analogous manner. As shown in FIG. 1, the first and second discharge lines 31 can extend further than the inlet line 2 or respectively outlet line 3. In other words, the end of the first and second discharge line 31 can be in contact with the cleaning device 8, for example with its base surface, but the end of the inlet line 2, or respectively outlet line 3, can be formed spaced apart form the base surface of the cleaning device 8.

In other words, also with the introducing of the connection element 1 in the cleaning device 8 with a flat base surface, a fluidic connection between first discharge line 21 and inlet line 2, or respectively second discharge line 31 and outlet line 3 is possible. As illustrated in FIG. 1, the connection element 1 has, furthermore, a middle section 4. From one end of the middle section 4 the inlet line 2 and the first discharge line 21 extend in a parallel manner in respectively two cylindrical projections 61, 62 which are spaced apart from one another. The other ends of the inlet line 2 and of the first discharge line 21 which are fluidically opposed to these projections 61, 62 extend substantially perpendicularly to these projections 61, 62 form the middle section 4 in a cylindrical first extension 51.

Figure 3:
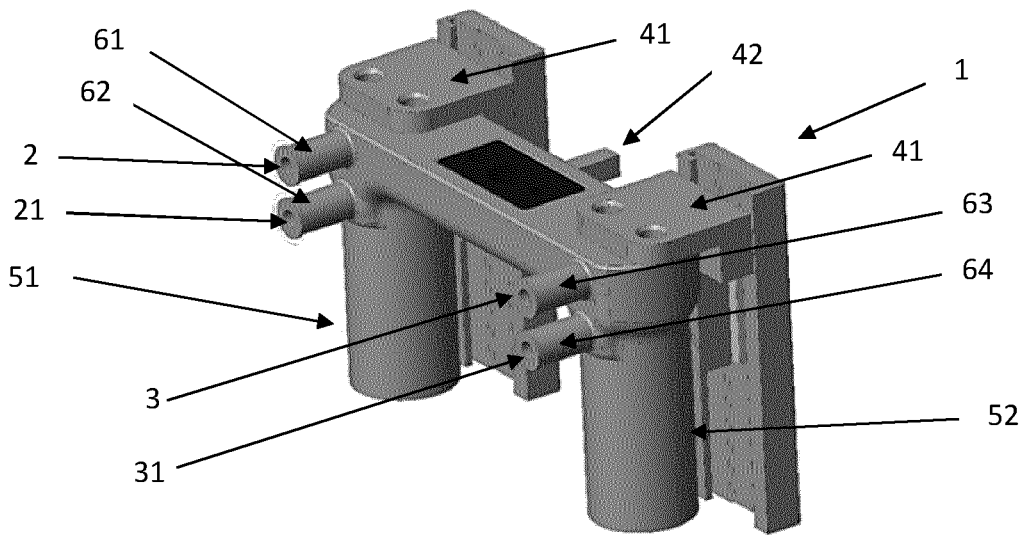
FIG. 3 a partial view of a connection system of a first embodiment.

In a corresponding manner, the outlet line 3 and second discharge line 31 are arranged at a second end of the middle section 4. As shown in FIG. 3, the connection element 1 can have guide elements 41. The guide elements 41 can be formed here integrally with the connection element 1. Alternatively, the guide elements 41, as shown in this embodiment, can be further structural elements which are able to be mounted on the connection element 1. For this, the guide elements 41 have through-bores with an internal thread, and the connection element 1 has at the first and second end blind bores with an internal thread. Hereby, the guide element 41 can be fastened to the connection element 1. Alternatively, the guide element 41 can be glued, rivetted or welded to the connection element 1.

As will be shown later, the guide elements 41 can arrange the connection element 1 movably with a guide structure 71 which is arranged in a housing 7. The connection element 1 can have, furthermore, a positioning element. In the embodiment shown in FIG. 3, the positioning element 42 is a projection extending from the middle element. By means of this positioning element, the position of the connection element 1 can be detected, by the connection element 1 interacting with a light barrier which is associated with the housing 7.

FIG. 3 shows a partial view of the connection system according to an embodiment of a connection system. The connection system can have a connection element 1 according to the previously described embodiment. Furthermore, the connection system has a housing 7. In the housing 7, connection guides 71 are arranged which, as shown in FIG. 3, are formed as two linear guides projecting from the housing inner wall. Via the previously described guide element 41, formed on the connection element 1, the connection element 1 can be moved linearly in the housing 7. The connection system has, furthermore, a drive unit 43. In this embodiment, the drive unit 43 for driving the connection element 1 is arranged outside the housing 7. Alternatively, however, the drive unit 43 can also be arranged in the housing 7. Four cylindrical projections (61, 62, 63, 64), preferably running parallel to one another, are provided.

The drive unit 43 here is an electric motor. In the middle section 4 of the connection element 1 a threaded nut is arranged. Furthermore, in the housing 7 a threaded spindle is arranged, which is in engagement with the threaded nut of the connection element 1. The threaded spindle is driven by the electric motor. For this, a toothed belt pulley, the driven toothed belt pulley, is arranged around the threaded spindle, for example in a press fit. A toothed belt is placed around the toothed belt pulley, via which toothed belt the power transmission takes place from the toothed belt pulley which is driven by the electric motor. FIGS. 4a and 4b show the guiding of the connection element 1 in the connection guides 71. Here, ball guide bushings are arranged in the housing 7, in which respectively the cylindrical first and second extensions 51, 52 are displaceably arranged. Alternatively, guide tracks 71, as shown in the embodiment in FIG. 5, for example made of aluminum, can be used, wherein here a guide carriage, for example made of plastic can be mounted on the connection element 1.

Figures 6A, 6B:
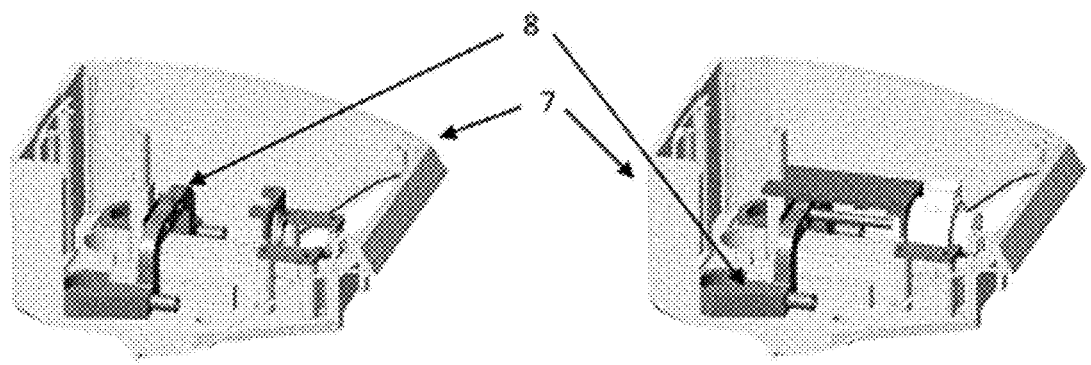
FIGS. 6a and 6b partial views of the cleaning device of the connection system.

In the housing, furthermore, a cleaning device 8 is movably arranged, as shown in FIGS. 6a and 6b. For this, cleaning guides 72 are formed in the housing 7 perpendicularly to the connection guides 71. For driving the cleaning device 8, a second drive unit 43 can be arranged in the housing 7. The threaded spindle, driven by the electric motor, as shown in FIG. 7b, engages into a threaded nut which is formed on the cleaning device 8.

Figures 7A, 7B:
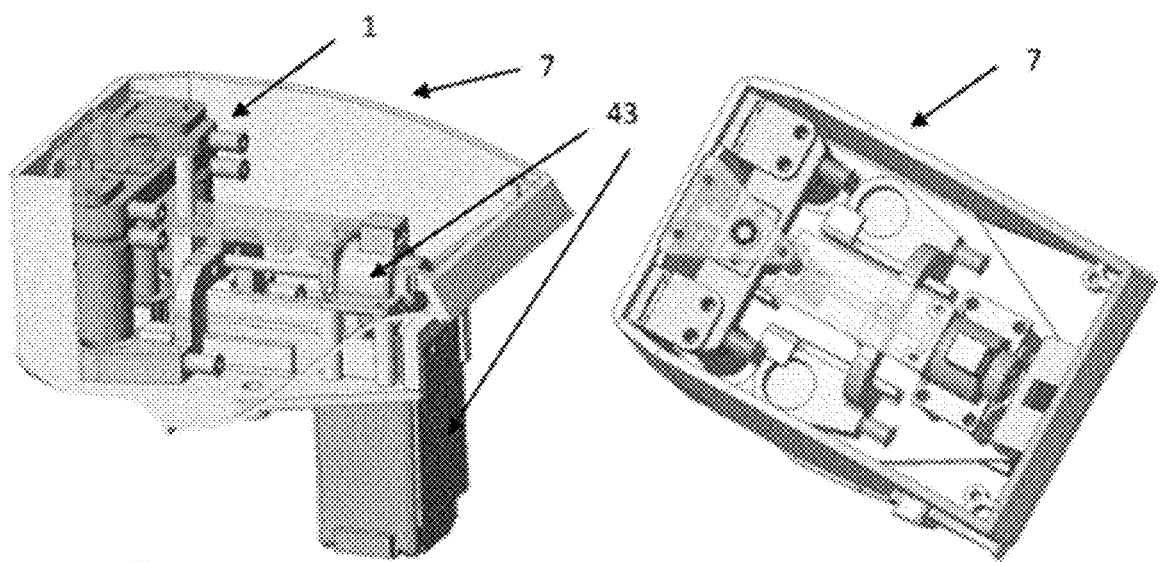
FIGS. 7a and 7b perspective views of the connection system according to the first embodiment.

FIGS. 7a and 7b show perspective views of the connection system according to the first embodiment, in particular the arrangement of the connection system. For actuating the drive unit 43 of the connection element 1 and cleaning device 8, a control unit can be arranged in the housing 7 or associated with the latter. Hereby, the connection element 1 is movable between several, preferably three positions. The determining of the position can take place via sensors and is realized in the embodiment shown here by light barriers in the housing 7, which can detect the positioning element of the connection element 1. The cleaning device 8 can also be moved between several, preferably two, positions. The determining of position of the cleaning device 8 can also take place via light barriers.

Figures 8A, 8B:
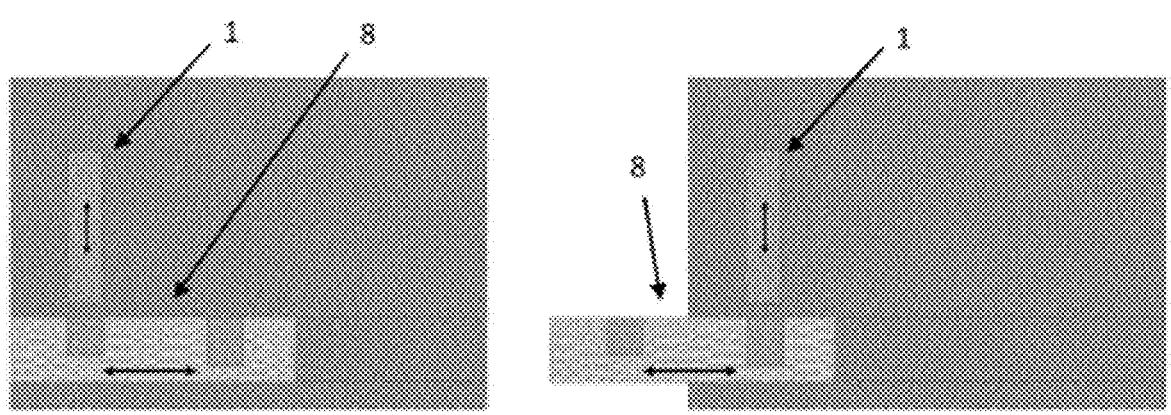
FIG. 8a, b a schematic diagram of degrees of freedom of a connection method according to a first embodiment.

In FIGS. 8a and 8b a schematic diagram is shown of degrees of freedom of a connection method according to a first embodiment. In FIG. 8a a state for achieving a connection position is shown. In this position, the connection element 1 can be moved vertically downwards, in order to thus engage into the cleaning device 8. In the connection position, the first and second extensions of the connection element 1 are connected with the concentrate bag, so that a fluidic connection is able to be formed via the inlet line 2, through the concentrate bag, and via the outlet line 3 back to the dialysis machine. In other words, in the connection position pure water is introduced out of the connection of the dialysis machine, provided for this, via the inlet line 2 of the connection element 1 into the concentrate bag, is mixed with the dry concentrate, in order to be subsequently fed to the dialysis machine again via the outlet line 3 of the connection element 1.

After the completion of the dialysis treatment, the connection element 1 moves out from the cleaning device 8 vertically into a waiting position. In this waiting position, the connection element 1 is not in engagement with the cleaning device 8. To form a cleaning position, the cleaning device 8 subsequently moves horizontally. The concentrate bag, which in this embodiment is mounted on the cleaning device 8, is moved with the cleaning device 8, in order to thus be able to be removed. Independently of the removal of the concentrate bag, the connection element 1 can move vertically into a cleaning position into the cleaning element 8. In the cleaning position, the first and second extensions are in engagement in line elements, which can be formed as blind holes in the cleaning device 8.

Figure 9:
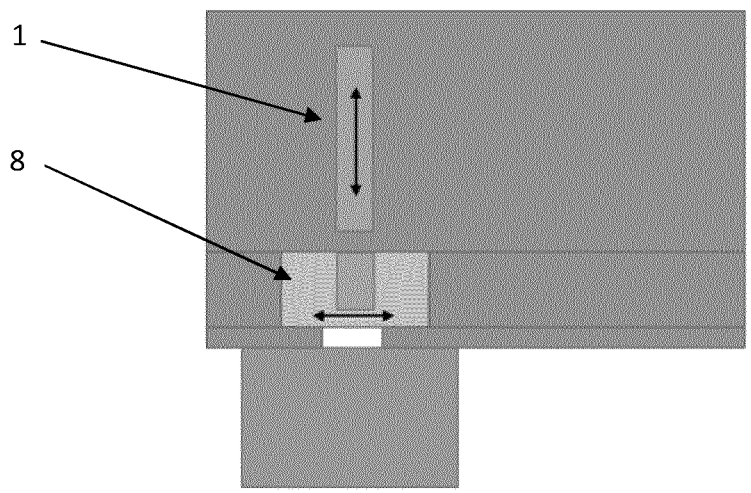
FIG. 9 a schematic diagram of degrees of freedom of a connection method according to a second embodiment.

In the cleaning position, a fluid flow can thereby be achieved in via the inlet line 2 and out via the first discharge line 21, and in an analogous manner, a fluid flow in via the outlet line 3 and out via the second discharge line 21. Hereby, a cleaning of the inlet line 2 and outlet line 3 takes place. In this cleaning position, the inlet line 2 and outlet line 3 can now be cleaned. FIG. 9 shows a further, second, embodiment as a schematic diagram of the movement sequences of the connection method. Here, the concentrate bag is not mounted on the cleaning device 8, in order to be able to move therewith. In this embodiment, the concentrate bag is mounted on the housing 7 by the nursing staff. To achieve the connection position, the cleaning device 8 moves horizontally, so that the connection element 1 can be moved vertically downwards and can thus be connected with the concentrate bag.

Figure 10:
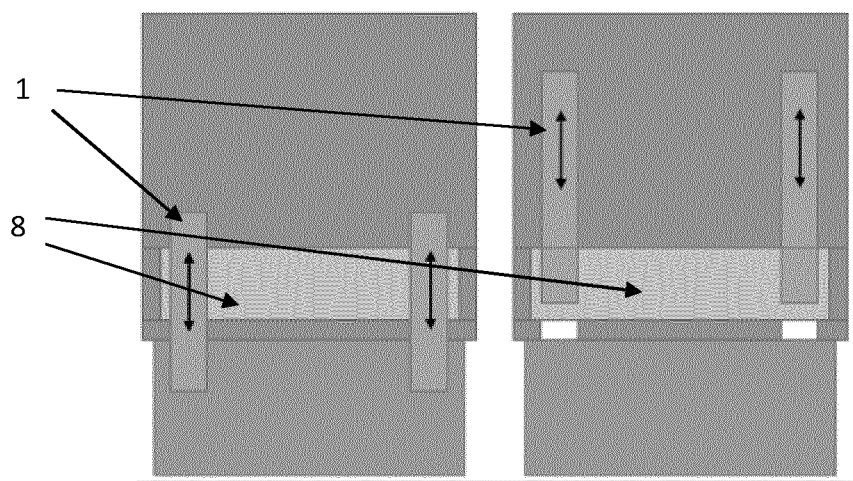
FIG. 10 a schematic diagram of degrees of freedom of a connection method according to the second embodiment.
Figures 11A, 11B:
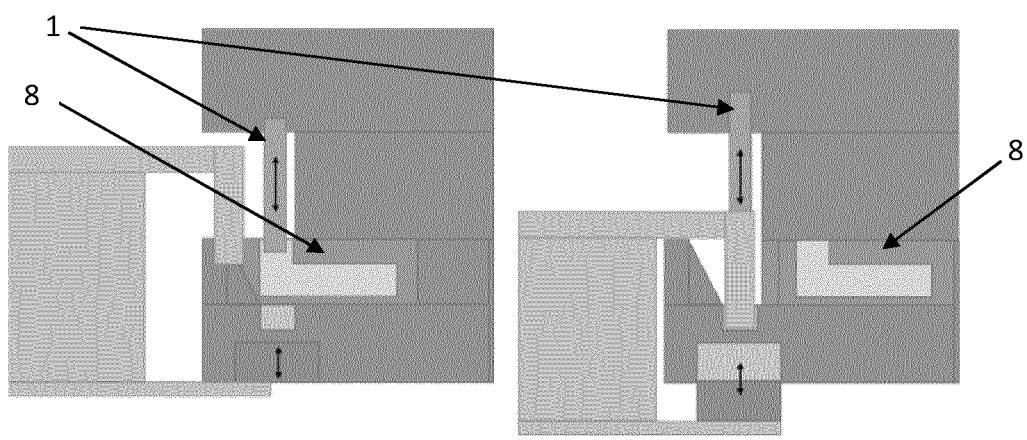
FIG. 11a, b a schematic diagram of degrees of freedom of a connection method according to a third embodiment.

After the dialysis treatment, the connection element 1 moves from the concentrate bag vertically upwards. The concentrate bag can now be removed by the nursing staff. Independently thereof, the cleaning device 8 moves horizontally under the connection element 1. Subsequently, the connection element 1 moves vertically in order to come in engagement with the cleaning device 8 and to thus form the cleaning position. FIG. 10 shows the connection method according to the second embodiment in a front view. FIGS. 11a and 11b show a further embodiment of the connection method. FIG. 11a shows here the cleaning position in which the connection element 1 is situated in the cleaning device 8. While the connection element 1 is situated in the cleaning position, a concentrate bag can be mounted on the housing 7. When the connection element 1 moves, after the cleaning, out from the cleaning device 8 vertically away from the latter, the cleaning device 8 can subsequently move horizontally.

Figures 12A, 12B:
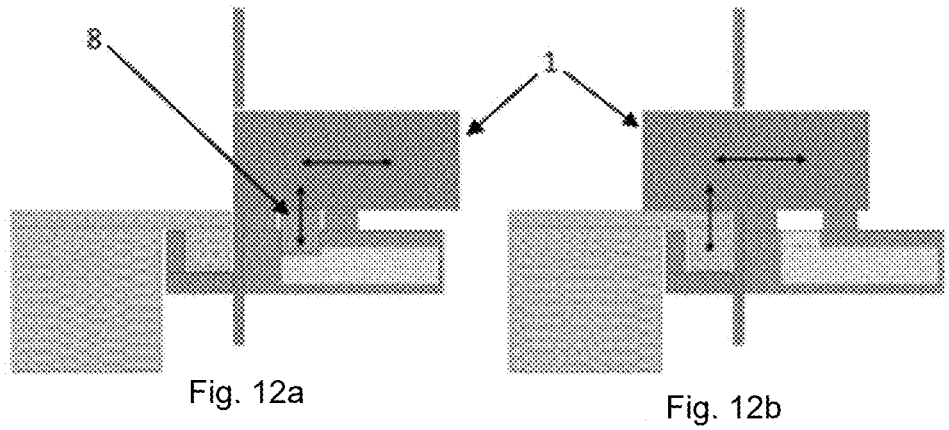
FIG. 12a, b a schematic diagram of degrees of freedom of a connection method according to a fourth embodiment.

Hereby, the position beneath the connection element 1 becomes free, whereby the concentrate bag is displaced, for example facilitated by an oblique feeding and/or a spring element. When the concentrate bag is situated beneath the connection element 1, this subsequently moves in order to assume a connection position, and thereby to be connected with the concentrate bag. FIG. 12a and FIG. 12b show a further schematic diagram of the movement sequence of the connection method. Here, the mount for the concentrate bag is arranged externally on the housing 7. The connection element 1, on the other hand, can be moved out from the housing 7. The cleaning device 8 is arranged beneath the connection element 1 in the housing 7. To achieve the connection position, the connection element 1 is moved horizontally out from the housing 7.

Subsequently, the connection element 1 can be moved vertically for engagement into the concentrate bag. Alternatively, the concentrate bag can be arranged displaceably on the housing 7, so that the concentrate bag can be displaced in the direction of the connection element 1. Subsequently, the connection element 1 is moved back again horizontally into the housing 7. In order to take up the cleaning position, the connection element 1 can be moved vertically into the cleaning device 8. Alternatively, the cleaning device 8 can be arranged in a vertically movable manner in the housing 7. Through an engagement of the connection element 1 with the cleaning device 8, the cleaning position is thus taken up.

Figures 13A, 13B, 13C:
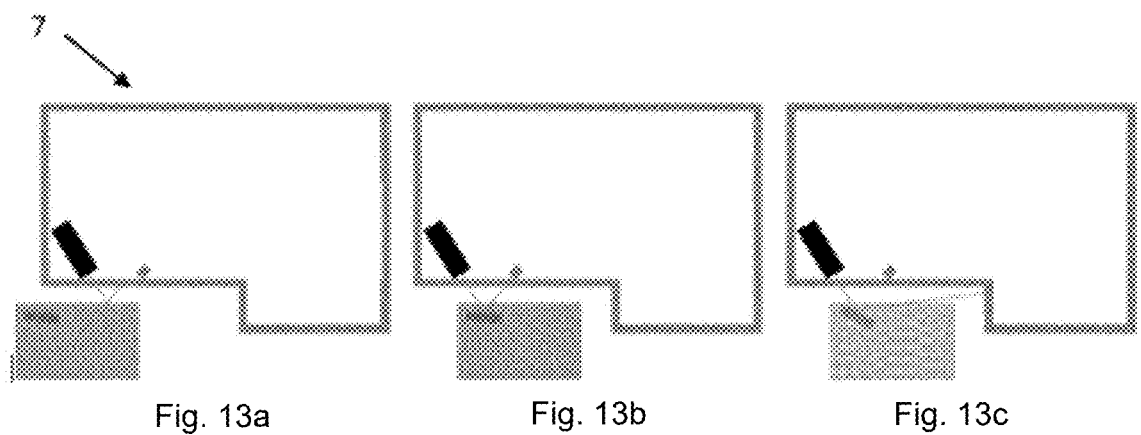
FIGS. 13a, 13b, and 13c schematic diagrams showing a method step for detecting a concentrate container.

To detect whether a concentrate bag is situated on the housing 7, the housing 7 can have a detection unit. For this, as is illustrated in the schematic diagrams shown in FIGS. 13a, 13b, and 13c, a light source can be formed as transmitter, and a light receiver can be formed on the housing 7. The transmitter and receiver can be formed here on an underside of the housing 7, under which the concentrate bag can be received. The concentrate bag has on a surface a reflection geometry. When the light source transmits a light beam in a particular direction, the light impulse is received in a corresponding intensity only at the light receiver when the concentrate bag is arranged at a predetermined position relative to the housing 7.

The reflection geometry on the concentrate bag can vary here, for example depending on the dry concentrate which is situated in the concentrate bag. Thereby, it is not only ensured that the concentrate bag is situated at the correct position, but rather it is also ensured that the dry concentrate, provided for a specific treatment, has been provided. When it is established that an incorrect concentrate bag is situated, or is situated in an incorrect position, in other words the reflection geometry is not detected by the receiving at the receiving unit, a start of treatment can be prevented. For example, the nursing staff can be presented with a notification, for example in the form of an alarm.

Figures 14A, 14B:
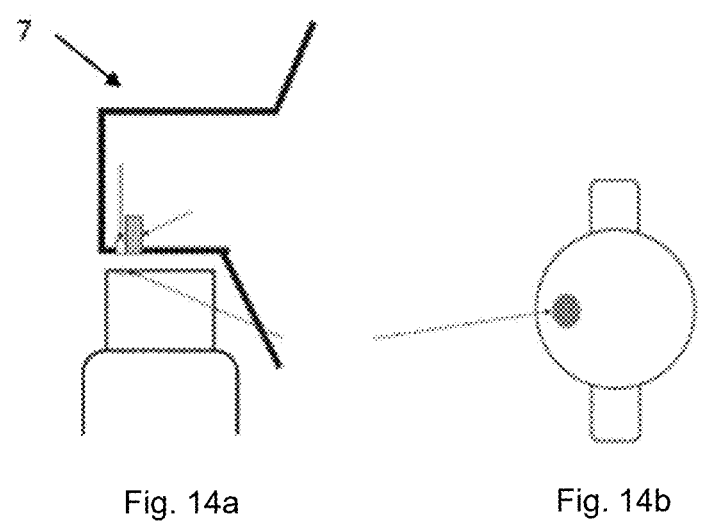
FIGS. 14a and 14b schematic diagrams showing a method step of an alternative detection of a concentrate container.

In a further embodiment, the housing 7 can have a color sensor as receiver and a light source as transmission unit. Accordingly, as in the schematic diagrams shown in FIGS. 14a and 14b, the concentrate bag can have a color marking. Here, according to colored coding, it can be detected which type of dry concentrate or which concentrate bag type is present. Likewise, a predefined filling quantity, and a correct positioning, can be detected. Also in this embodiment, the light source and colour color sensor can be formed on an underside of the housing 7. As a further embodiment, a radar sensor can be arranged on the housing 7, and the position and the presence of the concentrate bag can be detected.

Figures 15A, 15B:
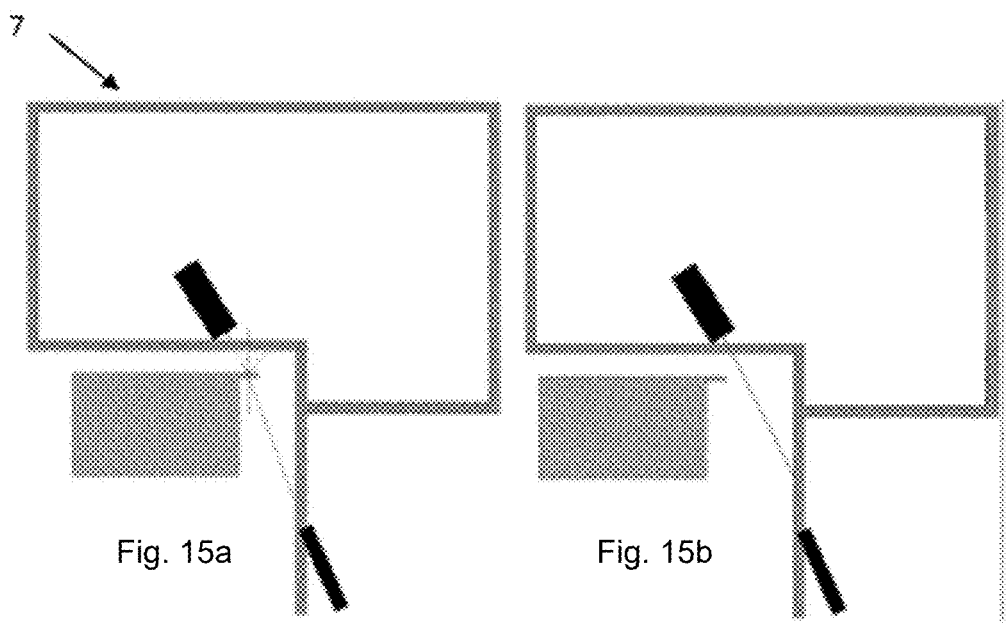
FIGS. 15a and 15b schematic diagrams showing a method step of a further detection of a concentrate container.

FIGS. 15a and 15b show schematic diagrams of a further embodiment of the detection unit. Also, in this embodiment, the housing 7 has a transmission-and receiving unit. The transmission unit here is a light source. The receiving unit is arranged on the housing 7 in such a way that it only receives a light impulse when the correct concentrate bag is situated at the correct position. This is ensured due to the characteristic refractive index of the material which is used..

Here, the refractive index of the concentrate bag is taken as the basis for the expected reflection angle. When at a correspondingly positioned receiving unit no previously defined light impulse is received, the previously mentioned conditions of the correct concentrate bag and/or position thereof are not fulfilled. The receiving unit can be formed here, as illustrated in FIGS. 15a and 15b, on a side of the housing 7 lying opposite the underside of the housing 7 at an angle.

Figures 16A, 16B, 16C:
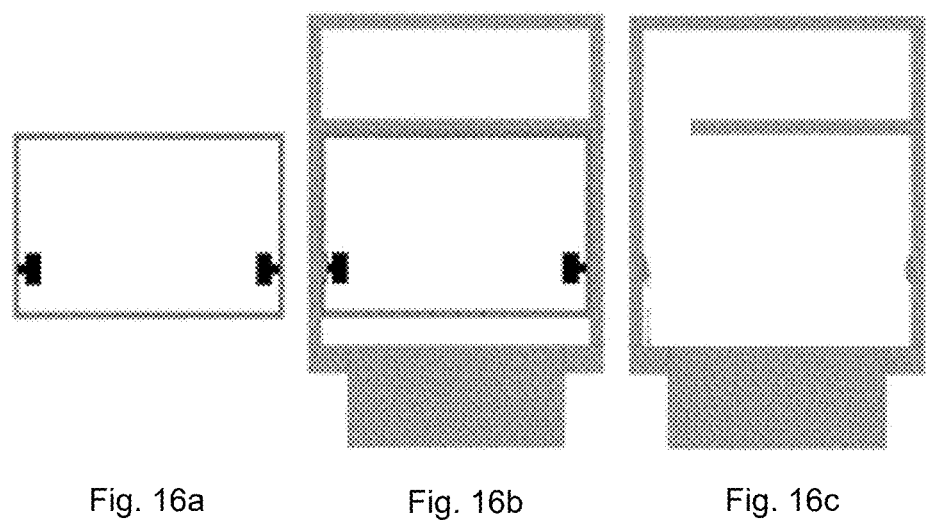
FIGS. 16a, 16b, and 16c schematic diagrams showing a method step of another detection of a concentrate container.

FIGS. 16a, 16b, and 16c show a further embodiment of the detection unit. Here, the housing 7 has at least one, but preferably several, microswitches, at a position at which the concentrate bag is situated in a correct position. As shown in FIGS. 16a, 16b, and 16c, the concentrate bag can have two projections. The microswitch on the side faces of the housing 7 can be arranged directly behind an elastomer layer, so that with a pressing-in of the latter by the projections, the microswitch is triggered. The coding of different concentrate bags can take place here by means of the position of the microswitches on the housing 7.

The invention claimed is:

1. A connection element for a blood treatment device, comprising
   an inlet line, for letting in a fluid into the connection element,
   an outlet line, for letting out a fluid from the connection element,
   at least a first discharge line, for discharging a fluid from the connection element,
   a middle section,
   a first extension, in which the first discharge line is formed around the inlet line, which extends from a first end of the middle section in a first direction from the middle section, and
   a second extension, in which a second discharge line is formed around the outlet line, which extends from a second end of the middle section lying opposite the first end of the middle section, in the first direction from the middle section, wherein
   the first discharge line is formed in a subsection around the inlet line, and
   the inlet line and the first discharge line are open to a first end section of the connection element, and the first end section is fluidically connected with the subsection.

2. The connection element according to claim 1, further comprising
   a second discharge line, for discharging a fluid from the connection element, wherein the second discharge line is formed in a second subsection around the outlet line,
   and wherein the outlet line and the second discharge line are open to a second end section of the connection element and the second end section is fluidically connected with the subsection.

3. The connection element according to claim 1, wherein the inlet line and/or outlet line and/or the first and second discharge line are arranged in the connection element in such a way that a deflection of the fluid direction in the connection element is able to be achieved.

4. The connection element according to claim 1, further having
   four cylindrical projections, wherein the inlet line and the first discharge line extend each in a projection from the first end of the middle section in a second direction which is different from the first direction, and wherein the outlet line and the second discharge line extend each in a projection from the second end of the middle section in the second direction.

5. The connection element according to claim 1, further having guide elements for the movable, connection with a guide device.

6. The connection element according to claim 1, further having a positioning element, which projects from the middle section in a third direction that is different from the first direction and different from the second direction.

7. A method comprising:
   forming a housing in a blood treatment device, with the connection element of claim 1, wherein the connection element is movable in the housing on a first straight line, which has two extensions, and with a cleaning element, movable in the housing on a second straight line, to the first straight line, in which a first and a second line element are formed, and
   moving the connection element on the first straight line for the formation of a cleaning position, wherein, in the cleaning position, the first and second extension of the connection element are in engagement with the first and second line element of the cleaning element.

8. The connection element according to claim 1, wherein the inlet line and/or outlet line and/or the first and second discharge line are arranged in the connection element in such a way that a deflection of the fluid direction in the connection element, by 120 to 70 degrees, is able to be achieved.

9. The connection element according to claim 1, wherein the inlet line and/or outlet line and/or the first and second discharge line are arranged in the connection element in such a way that a deflection of the fluid direction in the connection element, by 110 to 80 degrees, is able to be achieved.

10. The connection element according to claim 1, wherein the inlet line and/or outlet line and/or the first and second discharge line are arranged in the connection element in such a way that a deflection of the fluid direction in the connection element, by substantially 90 degrees, is able to be achieved.

11. The connection element according to claim 1, wherein the first extension extends from the first end of the middle section in a first direction substantially perpendicularly from the middle section, the second extension extends from a second end of the middle section lying opposite the first, in the first direction parallel to the first extension, from the middle section.

12. The connection element according to claim 1, further having four cylindrical projections running parallel to one another, wherein each of the inlet line and the first discharge line extends from the first end of the middle section in a second direction that is different from the first direction, and wherein
    the outlet line and the second discharge line extend each in a projection from the second end of the middle section in the second direction.

13. A connection system for a blood treatment device, comprising
    a connection element,
    a housing, in which the connection element is movably arranged,
    a cleaning element, which is movably arranged in the housing,
    at least a first drive unit, for moving the connection element and/or the cleaning element, and
    a control unit for activating the at least first drive unit, wherein
    the connection element comprises
    an inlet line, for letting in a fluid into the connection element,
    an outlet line, for letting out a fluid from the connection element,
    at least a first discharge line, for discharging a fluid from the connection element, and wherein the first discharge line is formed in a subsection around the inlet line, and the inlet line and the first discharge line are open to a first end section of the connection element, and the first end section is fluidically connected with the subsection.

14. The connection system according to claim 13, further comprising connection guides, which are arranged in the housing, on which the connection element is movable between several positions, cleaning guides, which are arranged in the housing, on which the cleaning element is movable between several positions.

15. The connection system according to Claim claim 13, further having at least one position sensor in the housing, by means of which the position of the connection element and/or of the cleaning element is able to be detected.

16. A connection method for the connection of a dry concentrate container, wherein a housing is formed with a connection element that is movable in the housing on a first straight line that has two extensions, and with a cleaning element that is movable in the housing on a second straight line that is substantially perpendicular to the first straight line, in which cleaning element a first and a second line element are formed, the connection element comprising an inlet line, for letting in a fluid into the connection element, an outlet line, for letting out a fluid from the connection element, at least a first discharge line, for discharging a fluid from the connection element, wherein the first discharge line is formed in a subsection around the inlet line, the inlet line and the first discharge line are open to a first end section of the connection element, and the first end section is fluidically connected with the subsection, said method comprising the steps of moving the connection element on the first straight line for the formation of a cleaning position, wherein in the cleaning position the first and second extension of the connection element are in engagement with the first and second line element of the cleaning element.

17. The connection method according to claim 16, further having moving of the connection element on the first straight line, moving the cleaning device on the second straight line, moving the connection element on the first straight line for the formation of the connection position, wherein in this connection position, the first and second extension project from the housing.

18. The connection method according to claim 16, further having mounting a container on the housing, when the connection element is in the cleaning position, detecting whether the container is provided for connection, moving the connection element on the first straight line into the connection position, connecting the container with the first and second extension of the connection element, so that a fluidic connection is produced.

19. The connection method according to claim 16, wherein the connection element is able to be fluidically connected to a blood treatment device, further having moving of the connection element on the first straight line in a first direction, moving the cleaning element on the second straight line, moving the connection element on the first straight line in an opposite direction to the first direction, for the formation of the cleaning position, so that the first and second extension are received respectively in the first and second line element of the cleaning device, cleaning the first and second extension in the first and second line element.

\* \* \* \* \*